United States Patent [19]

Kralick et al.

[11] Patent Number: 5,104,852
[45] Date of Patent: Apr. 14, 1992

[54] METHOD FOR THE INHIBITION OF THE PROLIFERATION OF CANCER CELLS IN A TUMOR SENSITIVE TO TREATMENT WITH A SELENODITHIOL BY THE INJECTION INTO THE TUMOR OF A SELENODITHIOL SUCH AS SELENODIGLUTATHIONE

[75] Inventors: Francis A. Kralick; Wayne B. Parrish; Darryl N. Willett, all of Columbus, Ohio

[73] Assignee: The Ohio State University, Columbus, Ohio

[21] Appl. No.: 643,360

[22] Filed: Jan. 22, 1991

Related U.S. Application Data

[63] Continuation-in-part of Ser. No. 316,018, Feb. 27, 1989, abandoned, and a continuation-in-part of Ser. No. 443,608, Nov. 30, 1989.

[51] Int. Cl.$^5$ ............................................. A61K 37/14
[52] U.S. Cl. ..................................../..................... 514/6
[58] Field of Search ........................................... 514/6

[56] References Cited

PUBLICATIONS

Vernie et al., "Studies on the Inhibition of Protein Synthesis by Selenodiglutathione", *Biochem Journal*, 180, 1979, pp. 213–218.
Vernie et al., "Inhibition of In Vitro Amino Acid Incorporation by Na$_2$SeO$_3$", *Journal Biol. Chem.*, 255, 1980, pp. 6913–6917.
Vernie et al., *Biochem. Biophys. Acta.*, 414, 1975, pp. 283–292.
A. M. Watrach et al., "Inhibition of Human Breast Cancer Cells by Selenium", *Cancer Letters*, 25, 1984, pp. 41–47.
Poirier and Milner, "Factors Influencing the Antitumorigenic Properties of Selenium", *J. Nutr.*, 1983.
Webber et al., "Inhibitory Effects of Selenium on the Growth of DU-145 Human Prostrate Carcinoma Cells In Vitro", *BioChemical and Biophysical Research Communications*, vol. 130, No. 2, 1985, pp. 603–609.
Medina et al., *Cancer Research*, 44, 1984, pp. 4361–4365.
Vendeland et al., "Transport of Selenium as Selenite or Selenomethionine Across Brush-Bordered Membranes from the Upper Intestines of Rats", *Chem. Abstracts* 0018549260—1943.
Ganther, *Biochemistry*, vol. 10, No. 22, pp. 4089–4098.
Vernie et al., "Studies on the Inhibition of Protein Synthesis by Selenodiglutathione", *Biochem Journal*, 180, 1979, p. 213.
Milner, "Selenium and Carcinogenesis", *American Chemical Society*, 1985, pp. 267–282.
Medina et al., "Uptake and Localization of Selenium-75 in Mammary Epithelial Cell Lines In Vitro", *Cancer Letters*, 15, 1982, pp. 301–310.
Vernie et al., "Inhibition of the Growth of Malignant Mouse Lymphoid Cells by Selenodiglutathione and Selenodicysteine", *Cancer Letters*, 14(3), 1981, pp. 303–313.
Ip and Clement, "Factors Influencing the Anticarcinogenic Efficacy of Selenium in DMBA-Induced Mammary Tumorigensis in Rats", *Cancer Research*, 41, 1981, pp. 2683–2686.
Fico et al., "Differential Effects of Se on Normal and Neoplastic Canine Mammary Cells", *Cancer Res.*, 46, 1986, pp. 3384–3388.
Khalil et al., "5-Bromodeoxyuridine— and N-Methyl-N-Nitrosourea–Induced Sister Chromatid Exchanges Correlate with Reduced Survival Not Cell Kinetics of Cultured Human Lymphocytes"—1984.

*Primary Examiner*—Jerome D. Goldberg
*Assistant Examiner*—T. J. Criares
*Attorney, Agent, or Firm*—Frank H. Foster

[57] ABSTRACT

The invention discloses a biphasic method of treating cancer tumors sensitive to treatment with selenodithiols, which method comprises administering a specific amount of a selenodithiol to the cancer tumor whereby the cancer tumor cells die and the surrounding non-cancerous tissue exhibits cell proliferation in cells sensitive to selenodithiols. A range of ratios of selenodithiol concentration to tumor diameters or volume is claimed.

8 Claims, 8 Drawing Sheets

|  | DAY 1 | DAY 8 | DAY 15 | DAY 23 | DAY 30 | DAY 38 | DAY 44 | DAY 51 | DAY 58 | DAY 65 | DAY 72 | DAY 79 |
|---|---|---|---|---|---|---|---|---|---|---|---|---|
| CONTROL |  |  |  |  |  |  |  |  |  |  |  |  |
| # ANIMALS | 50 | 50 | 50 | 50 | 50 | 49 | 49 | 49 | 49 | 49 | 49 | 49 |
| # WITH TUMOR | 0 | 0 | 0 | 0 | 0 | 1 | 4 | 6 | 10 | 15 | 16 |  |
| AVERAGE WEIGHT | 180.0 | 202.8 | 209.9 | 213.0 | 217.7 | 224.8 | 227.0 | 224.2 | 226.0 | 241.9 | 253.8 | 241.1 |
| RETINOL (HPR) |  |  |  |  |  |  |  |  |  |  |  |  |
| # ANIMALS | 10 | 9 | 9 | 9 | 9 | 9 | 9 | 9 | 9 | 9 | 9 | 9 |
| # WITH TUMOR | 0 | 0 | 0 | 0 | 0 | 0 | 0 | 0 | 0 | 0 | 0 |  |
| AVERAGE WEIGHT | 152.0 | 139.4 | 152.0 | 172.0 | 183.4 | 196.8 | 201.3 | 197.8 | 204.3 | 204.3 | 204.3 | 212.9 |
| 1μg/g GSSeSG+HPR |  |  |  |  |  |  |  |  |  |  |  |  |
| # ANIMALS | 10 | 10 | 10 | 10 | 10 | 10 | 10 | 10 | 9 | 9 | 9 | 9 |
| # WITH TUMOR | 0 | 0 | 0 | 0 | 0 | 0 | 0 | 0 | 0 | 0 | 0 |  |
| AVERAGE WEIGHT | 147.0 | 133.0 | 146.7 | 167.7 | 172.1 | 189.9 | 201.5 | 191.7 | 177.1 | 188.4 | 196.3 | 194.9 |
| 2μg/g GSSeSG+HPR |  |  |  |  |  |  |  |  |  |  |  |  |
| # ANIMALS | 10 | 10 | 9 | 9 | 9 | 9 | 7 | 7 | 6 | 6 | 5 | 3 |
| # WITH TUMOR | 0 | 0 | 0 | 0 | 0 | 0 | 0 | 0 | 0 | 0 | 0 |  |
| AVERAGE WEIGHT | 152.0 | 139.5 | 147.7 | 172.5 | 175.3 | 185.7 | 201.3 | 192.5 | 200.5 | 201.7 | 208.3 | 209.0 |
| 2μg/g GSSeSG |  |  |  |  |  |  |  |  |  |  |  |  |
| # ANIMALS | 10 | 10 | 8 | 7 | 7 | 7 | 4 | 4 | 3 | 3 | 1 | 1 |
| # WITH TUMOR | 0 | 0 | 0 | 0 | 0 | 0 | 0 | 0 | 0 | 0 | 0 |  |
| AVERAGE WEIGHT | 175.1 | 189.9 | 200.4 | 215.4 | 216.7 | 219.1 | 234.2 | 215.3 | 233.7 | 239.2 | 224.1 | 235.0 |
| 1μg/g GSSeSG |  |  |  |  |  |  |  |  |  |  |  |  |
| # ANIMALS | 10 | 10 | 10 | 10 | 10 | 10 | 10 | 9 | 9 | 9 | 7 | 7 |
| # WITH TUMOR | 0 | 0 | 0 | 0 | 0 | 1 | 1 | 1 | 1 | 1 | 1 |  |
| AVERAGE WEIGHT | 182.0 | 194.6 | 202.5 | 215.8 | 217.8 | 221.9 | 215.7 | 221.8 | 219.3 | 220.1 | 222.8 | 222.5 |

FIG 3

METHOD FOR THE INHIBITION OF THE PROLIFERATION OF CANCER CELLS IN A TUMOR SENSITIVE TO TREATMENT WITH A SELENODITHIOL BY THE INJECTION INTO THE TUMOR OF A SELENODITHIOL SUCH AS SELENODIGLUTATHIONE

This invention is a Continuation-in-Part of the application filed on Feb. 27, 1989 with U.S. Ser. No. 07/316,018 titled "Method For The Inhibition of Cancer Cell Proliferation By The Utilization of Selenodithiols Such As Selenodiglutathione", and a Continuation-in-Part of the application filed on Nov. 30, 1989, U.S. Ser. No. 07/443,608 pending, titled "Method For The Stimulation Of Cell Growth And The Inhibition Of Cell Proliferation By The Utilization Of Selenodithiols Such As Selenodiglutathione".

TECHNICAL FIELD

This invention relates to medical treatments for the inhibition of cancer cell proliferation in mammalian host organisms. More specifically, this invention relates to a method for the injection into a tumor comprising cancer cells sensitive to treatment with a selenodithiol a specific concentration of the selenodithiol, whereby the proliferation of the cancer cells is inhibited without adverse effect on the non-cancerous tissue surrounding the tumor.

BACKGROUND ART

Cancer is one of the most significant causes of death in the world, accounting for approximately 20% of all deaths in humans. The disease, as is commonly well known, can effect persons of all ages, background, and socio-economic status.

There have been a variety of attempts in the prior art which indicate that selenium compounds can exhibit both anticarcinogenic and antimutagenic potential in both in vitro and in vivo systems.

An article by Vernie et al., "Studies on the Inhibition of Protein Synthesis by Selenodiglutathione", *Biochem Journal*, 180, 1979, pp. 213-218, discloses that GSSeSG is substantially more effective in inhibiting protein synthesis than sodium selenite ($Na_2SeO_3$) or oxidized glutathione; more particularly, in a cell-free system derived solely from rats, GSSeSG blocks amino acid incorporation through the inactivation of elongation factor 2 (EF-2). Also, the particular concentrations of GSSeSG utilized (4µg/ml) are significantly different than the concentrations utilized by applicants. Additionally, neither the binding of aminoacyltRNA to the ribosomes by elongation factor 1, nor the peptidyltransferase reaction, nor the ribosomes per se were affected. The reference further discloses (p. 218) that the inhibition of protein synthesis of cells in tissue culture opens a new perspective on counteracting tumor cells with selenium-type compounds of the general formula RSSeSR.

Another article by Vernie et al., "Inhibition of in vitro amino acid incorporation by Sodium Selenite", in *Biochemistry*, Vol. 13, No. 2, 1974, pp. 337-341 discloses that Selenite concentrations of $1.1 \times 10^{-5}$ M can inhibit EF-2, and the author's earlier work, Vernie et al., *Biochem. Biophys. Acta.*, 414, 1975, pp. 283-292, discloses that EF-2 is the target of the reaction product between $Na_2SeO_3$ and glutathione in the inhibiting of amino acid incorporation in vitro.

An article by A. M. Watrach et al., "Inhibition of Human Breast Cancer Cells by Selenium", Cancer Letters, 25, 1984, pp. 41-47, discloses that the parenteral administration of sodium selenite ($Na_2SeO_3$) completely inhibits the development of cancerous tumors in mice. The article further indicates that selenium can be transported by the host from a distant administration site to the site of the tumor, where it accumulates within and exerts its inhibiting effect upon cancer cell mitosis.

An article by Poirier and Milner, "Factors Influencing the Antitumorigenic Properties of Selenium", *J. Nutr.*, 1983, teaches that the intermediate products of selenium metabolism, such as GSSeSG, are as effective as selenite. However, the article does not disclose the non-toxicity of GSSeSG and also that GSSeSG is not as mutagenic as $Na_2SeO_3$.

An article by Webber et al., "Inhibitory Effects of Selenium on the Growth of DU-145 Human Prostate Carcinoma Cells In Vitro", *BioChemical and Biophysical Research Communications*, Vol. 130, No. 2, 1985, pp. 603-609, discloses that selenium, when administered as sodium selenite, inhibits the growth of human prostate carcinoma cells in vitro, as well as in other types of cancer cells. The reference further indicates that selenium can inhibit both the initiation and promotion stages of carcinogenesis (p. 607) and that selenium inhibits DNA synthesis, as reported by Medina et al., *Cancer Research*, 44, 1984, pp. 4361-4365.

Vendeland et al., "Transport of Selenium as Selenite or Selenomethionine Across Brush-Border Membranes From the Upper Intestines of Rats", *The FASEB Journal*, Vol. 2, No. 6, Abstract 7692, 1988, p. A1621 (Vendeland et al.), discloses an abstract entitled the "Transport of Selenium As Selenite Or Selenomethionine Across Brush-Bordered Membranes From the Upper Intestines of Rats".

The GSSeSG utilized was prepared by modifying a variation in the method of Ganther, reported in *Biochemistry*, Vol. 10, No. 22, pp. 4089-4098, and improved by Vernie et al., (See cite supra), page 213.

An article by Milner entitled "Selenium and Carcinogenesis", *American Chemical Society*. 1985, pp. 267-282, discloses that the anticarcinogenic property of selenium does not appear to be mediated through its association with glutathione peroxidase activity. Selenium is further disclosed as being effective in inhibiting the proliferation of neoplastic cells, and that GSSeSG, or other intermediate compositions which occur during selenium metabolism, are suggested as responsible for the antitumorigenic properties of this element. The diagram on page 278 describes a flow diagram of selenium metabolism which proceeds through GSSeSG.

An article by Medina et al., "Uptake and Localization of Selenium-75 in Mammary Epithelial Cell Lines In Vitro", Cancer Letters, 15, 1982, pp. 301-310, discloses that selenium can inhibit the growth potential of chemical carcinogen-induced tumorigenesis in mice.

A later article by Vernie et al., "Inhibition of the Growth of Malignant Mouse Lymphoid Cells by Selenodiglutathione and Selenodicysteine", *Cancer Letters* (Shannon, Irel) 14(3), 1981, pp. 303-313, discloses that intraperitoneal injections of GSSeSG or selenodicysteine in mice, which had been previously inoculated with tumor cells, inhibited the tumor growth and increased the life span of the animals as compared with the untreated control mice.

An article by Clement Ip, "Factors influencing the anticarcinogenic efficacy of selenium in DMBA-induced mammary tumorigenesis in rats", *Cancer Research*, 41, 1981, pp. 2683-2686, teaches that dosages of $Na_2SeO_3$ given to rats on low fat diets decrease tumorigenesis, but high fat fed animals did not respond as favorably. The results suggested that selenium has no effect on the proliferation of malignant vs. benign lesions.

An article by Fico et al., "Differential effects of Se on normal and neoplastic canine mammary cells", *Cancer Res.* 46, 1986, pp. 3384-3388, describes the differential effects of Se on normal and neoplastic canine mammary cells.

An article by Khalil et al., "5-Bromodeoxyuridine- and N-Methyl-N-Nitrosourea- Induced Sister Chromatid Exchanges Correlate With Reduced Survival Not Cell Kinetics Of Cultured Human Lymphocytes", disclosed that Sister Chromatid Exchange techniques can be utilized to determine the mutagenicity of GSSeSG.

Although it is clear that the prior art has attempted a variety of processes which have shown a certain amount of effectiveness in the treatment of carcinogenic cells through the utilization of selenium-containing compounds, these efforts have been unable to effectively destroy cancer cells without also damaging the treated host organism.

Accordingly, it is an object of the invention to provide a process for the utilization of selenium containing compounds which create a toxic crisis in the cancerous cells within a tumor, while also providing a non-toxic environment for the normal host cells surrounding the tumor. The process provided herein identifies a ratio of the concentration of selenodithiol injected into a cancer tumor per volume of cancer tumor whereby the cancer cells sensitive to treatment with a selenodithiol are killed and the noncancerous tissue surrounding the tumor is caused to grow.

It is another object of the invention to provide a process which utilizes a small genus of selenodithiols, and particularly GSSeSG, to effectively inhibit tumor cell proliferation in both humans and other animals.

Still another object of the present invention is the stimulation of cell growth of non-cancerous tissue by the administration of specific amounts of a selenodithiol. This embodiment of the biphasic effect of the present invention can be useful for the development of non-cancerous cell growth simultaneous with the inhibition of cancer cell proliferation in cancer cells sensitive to treatment with the selenodithiol.

By "biphasic effect" herein is meant the combination of enhanced cellular activity in cells sensitive to treatment with a selenodithiol which have been treated with a selenodithiol at a concentration below about $10^{-6}$ M and the decreased cellular activity and/or death in cells sensitive to treatment with a selenodithiol which have been treated with the selenodithiol at a concentration above about $10^{-5}$ M.

BRIEF DESCRIPTION OF INVENTION

The invention comprises a method for the inhibition in a cancer tumor in a host organism of cancer cell proliferation in cancer cells sensitive to treatment with a selenodithiol, comprising administering an effective amount of a selenodithiol or its pharmaceutically acceptable salts for a sufficient time to the cancer tumor. In particular, the selenodithiol GSSeSG, when present in concentrations ranging from about $10^{-6}$ M to about $10^{-5}$ M effectively inhibits cancer cell proliferation in cells sensitive to treatment with selenodithiol in the treated host without significant toxicity to the non-cancer cells of the host organism. "Administration" as used herein includes direct injection, cannulation, or an equivalent application to a cancer tumor to be treated.

BRIEF DESCRIPTION OF DRAWINGS

Various other objects, features and attendant advantages of the present invention will be more fully appreciated when considered in connection with the accompanying drawings wherein:

FIG. 3 provides the results obtained from treating each of five groups of rats, which were previously inoculated with a chemical carcinogen and were then subsequently tested with different dosages of cancer treating agents, including GSSeSG, and further comparing the results with a control group of cancer infected but untreated rats.

Figure 1:
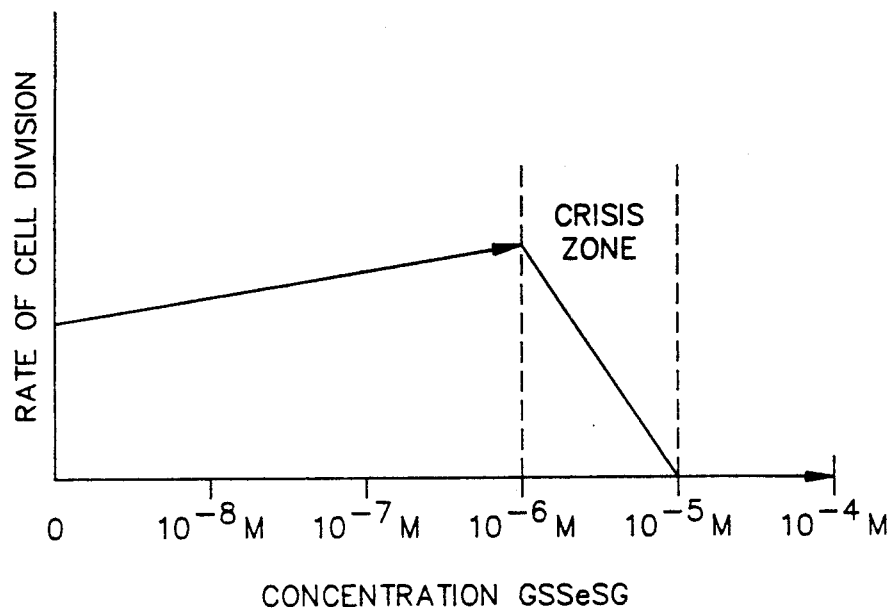
FIG. 1 provides a plot measuring neoplastic cell division or cell protein synthesis as a function of the concentration of the preferred selenodithiol, GSSeSG.

In describing the preferred embodiment of the invention which is illustrated in the FIGS., specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

The invention, in particular, relates to the utilization of a small genus of selenodithiol compounds which includes selenodimethionine and selenodicysteine and particularly selenodiglutathione (GSSeSG), which are capable of preventing in a cancer tumor the cancer cells sensitive to treatment with a selenodithiol from proliferating, while being substantially non-toxic to the cells surrounding the tumor in the mammalian host organism being treated, including humans. This surprising discovery has been demonstrated by both extensive in vivo rat data as well as in vitro experiments on human neoplastic and non-neoplastic cells, including fibroblasts and keratinocytes.

More particularly, a biphasic effect can be seen with increasing concentrations of GSSeSG. The first stage of this biphasic effect results in so-called "crisis zone" in which the growth of the cancer cells sensitive to treatment with a selenodithiol is substantially terminated within a particularly narrow range of selenodithiol concentrations, and, surprisingly, without significant damage to the host organism being treated. More particularly, at concentrations less than the critical range, i.e., less than about $10^{-6}$ M, the proliferation of the non-cancerous cells surrounding the cancer tumor increases during the second stage of the biphasic effect. Thus as the cancer tumor is treated with, for example, GSSeSG, but within this narrow range, the cancer cells sensitive to treatment are substantially eliminated, while the surrounding non-cancerous cells sensitive to treatment proliferate.

In the copending parent application filed on Feb. 27, 1989 with U.S. Ser. No. 07/316,018, applicant has claimed a method for the biphasio treatment of cancer cells and surrounding tissue in a mammal, wherein a first phase of the biphasic treatment comprises the administration to a site of cancer cells in the mammal of a selenodithiol selected from the group consisting of selenodiglutathione, selenodicysteine, and selenodimethionine at a concentration above about $10^{-6}$ M, whereby proliferation of the cancer cells sensitive to treatment with the selenodithiol is inhibited, said selenodithiol radiating outwardly from said site by diffusion, and wherein a second phase of the biphasic treatment comprises the outwardly radiating diffusion of said selenodithiol in the cancer cells to said surrounding tissue of the mammal, wherein the concentration of the selenodithiol in the second phase in said surrounding tissue is reduced by the diffusion to a concentration below about $10^{-6}$ M, whereby proliferation of the cells sensitive to treatment with the selenodithiol in said surrounding tissue is enhanced, and whereby the mammal is not adversely effected by said biphasic treatment.

The present invention is directed to a method of treating cancer tumors sensitive to treatment with a selenodithiol selected from the group consisting of selenodiglutathione, selenodicysteine, and selenodimethionine, wherein the method comprises administering an effective amount of the selenodithiol directly into the central region of a cancer tumor, wherein the effective amount of the selenodithiol is an amount sufficient to achieve an initial concentration in the tumor of from about $10^{-3}$ milligrams of selenodithiol per milliliter of aqueous solution administered per 1.5 centimeters of cancer tumor diameter to about $10^{-3}$ milligrams of selenodithiol per milliliter of aqueous solution administered per 2.5 centimeters of cancer tumor diameter, wherein the numerator is the concentration of selenodithiol in milligrams per milliliter of administered aqueous solution, and the denominator is the average of the cancer tumor's major and minor axis lengths measured in centimeters, whereby the selenodithiol diffuses outwardly through the tumor from the central site of injection to the periphery of the tumor, and further diffuses into the surrounding non-cancerous tissue at a concentration of less than about $10^{-6}$ M.

It has been discovered that both the diffusion and absorption rates of the selenodithiol in the cancer tumor are constant. The absorption rate of the selenodithiol in the cancer tumor is related to the volume of tumor mass traversed by the diffusing selenodithiol. By approximating the volume of the cancer tumor according to the formula $V = 4/3 (3.14) r^3$, one can determine the toxic amount of selenodithiol to be injected into the tumor's central region so that upon diffusion outwardly toward the cancer tumor's boundary or periphery, the concentration of selenodithiol is reduced by dilution to a desirable level. If the initially injected amount is selected according to the present invention, the concentration of selenodithiol attained at the cancer tumor's periphery and beyond is less than or equal to about $10^{-6}$ M, at which level or below the selenodithiol causes cell proliferation in cells sensitive to selenodithiol treatment. This is due to the biphasic effect of the selenodithiol treatment discussed above.

The present invention therefore defines the limits of the initially injected dosage of the selenodithiol in a relationship to the cancer tumor's volume, or more simply, the tumor's average diameter. It has been discovered that if the average of the tumor's longest and shortest diameters is between 1.5 centimeters and 2.5 centimeters, the initially injected dosage of selenodithiol useful to achieve the present invention is $10^{-3}$ milligrams of selenodithiol per milliliter (mg/ml) of aqueous solution injected. Cancer tumors larger or smaller than 1.5 centimeters to 2.5 centimeters can similarly be treated by increasing or decreasing, respectively, the amount of selenodithiol initially injected into the central region of the cancer tumor, as long as the ratio of selenodithiol concentration to tumor diameter is maintained in the range prescribed above.

Thus according to the formula $V\ 4/3(3.14)r^3$, the volume of the cancer tumor which is to be centrally injected with the $10^{-3}$ mg/ml of initial selenodithiol is determined below:

$$V = 4/3\ (3.14)\ r^3$$
$$= 4/3\ (3.14)\ (1.5/2)^3 \text{ to } 4/3\ (3.14)\ (2.5/2)^3$$
$$= 1.76\ cm^3 \text{ to } 8.18\ cm^3$$

A ratio range of $10^{-3}$ mg of selenodithiol per ml of injected aqueous fluid per 176 cm$^3$ of tumor to $10^{-3}$ mg of selenodithiol per ml of injected aqueous fluid per 8.18 cm$^3$ of cancerous tumor is therefore preferred in the present invention.

If the cancer tumor diameter is between about 1.5 centimeters and 2.5 centimeters and a selenodithiol selected from the group consisting of selenodicysteine, selenodimethionine, and selenodiglutathione is injected at a concentration of $10^{-3}$ M centrally into a cancer tumor comprising cells sensitive to treatment with selenodithiols, the central regions of the tumor will die. As the selenodithiol diffuses into the non-cancerous tissue surrounding the tumor, the concentration will have decreased to $10^{-6}$ M or less and the surrounding tissue will be induced thereby to exhibit cell proliferation in cells sensitive to treatment with selenodithiols.

Direct injection or cannulation into the central region of the cancer tumor is crucial to the present invention. If the injection is at one edge of the tumor, the outward diffusion from the injection site will produce a toxic level of selenodithiol in the non-cancerous surrounding tissue, resulting in undesirable death of the tissue. Oral, nasal, or intravenous administration is also not acceptable in the present invention because of the toxic effect of the selenodithiol on the esophageal, mucosal or stomach cells.

The present invention allows for the direct treatment of cancer tumors which are inoperable due to location or size. A cancer tumor comprising cells sensitive to treatment with selenodithiol can be injected according to the present invention and caused to die without adverse effect on the surrounding non-cancerous tissue or the host organism It has been observed in treating cancer tumors according to the present invention that when an initial concentration is injected which is below the presently claimed ratio, the tumor will be caused to fold in on itself as the central portion of the tumor dies and the outer extremes proliferate. Thus if the cancer tumor is initially large, and the amount of selenodithiol injected is below the range of $10^{-3}$ mg/ml per 1.5 to 2.5 cm of tumor diameter, the result may be apparent overall growth of the tumor as the tumor periphery is caused to proliferate as the cells therein sensitive to treatment with selenodithiols exhibit growth stimulation. This may be observed in spite of the death of the cells sensitive to treatment with selenodithiols in the tumor's central region. However, if the dosage of selenodithiol injected is increased to within the range claimed herein, the cancer tumor comprising cells sensitive to treatment with selenodithiols will become hardened, shriveled and die, while the surrounding noncancerous tissue is stimulated to grow.

Conversely, if the initial selenodithiol concentration exceeds the claimed range of initial ratio of dosage to tumor diameter, death of the surrounding normal tissue, or even host death, will occur.

Thus the present invention describes the relationship between the tumor size and the amount of selenodithiol required to achieve the desired biphasic effect. This allows one administering the selenodithiol to the cancer tumor to determine the effective amount of selenodithiol to be administered by measuring the length and width of the tumor. If the initial concentration of the selenodithiol aqueous solution centrally injected into the cancer tumor comprising cells sensitive to treatment with selenodithiol is within the range prescribed by the above relationship between the average tumor diameter and the injected dosage, the outward diffusion through the tumor will dilute the selenodithiol concentration to such an extent that when the selenodithiol has diffused to the outer periphery of the cancer tumor, the concentration is less than about $10^{-6}$ M At concentrations less than about $10^{-6}$ M in cells sensitive to treatment with the selenodithiol, the selenodithiol promotes or increases cell proliferation.

It is known that toxins such as diphtheria toxin can catalyze the transfer of the ADP-ribosyl moiety of nicotinamide adenine dinucleotide (NAD) onto the elongation factor 2 (EF-2), thereby inhibiting protein synthesis in eucaryotic cells. The invention relates to the fact that selenodithiols which are selected from a small class of compounds, and particularly GSSeSG, appear to inhibit the EF-2 at least in the same mode as the diphtheria toxin.

The role of the EF-2 is that it drives the synthesis of the protein being formed in the desired direction through the two initiation sites, A and P, present on the ribosomes. The EF-2 governs the particular elongation of the protein to be formed in that the mRNA, selects the precise order of the amino acids to proceed through the A and P sites to form the resulting protein.

The invention particularly relates to GSSeSG and its pharmaceutically acceptable salts, the structure of GSSeSG being set forth below:

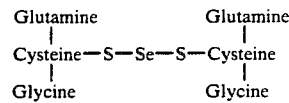

It is believed that GSSeSG inhibits the EF-2 factor through the creation of a biphasic effect of selenium on the cellular growth of the cancer cells. GSSeSG is, as seen above, a hexapeptide made from glutamine, cysteine and glycine, in which the cysteine moiety contains an —SH group which, it is hypothesized, aligns with the selenium on a corresponding glutathione molecule to form a linear structure, although applicants do not wish to be bound by theory with respect to a particular mechanism of operation. In the broadest embodiment, it is believed that the growth or proliferation of any cell containing EF-2 can be inhibited by GSSeSG administered at levels of $10^{-6}$ M to $10^{-5}$ M, and any cell containing EF-2 can be stimulated to grow by the GSSeSG administered at levels of less than about $10^{-6}$ M. Thus the present invention is effective in all eucaryotic cells, including but not limited to, mammalian neoplasms and chemically induced as well as naturally induced cancerous cells.

It is interesting to compare the structure of GSSeSG with glutathione in its reduced form, the structure of which is shown below,

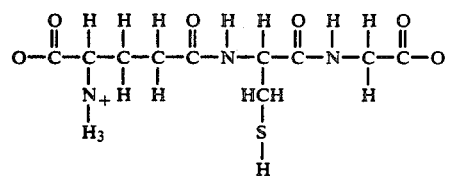

wherein the cysteine moiety contains the sulfur atom. It has been hypothesized that selenium can effectively substitute itself for the hydrogen bonded to the sulfurs, although as cited, supra, applicants do not wish to be bound by theory.

It should be noted that the R groups in the genus of selenodithiols can include substantially all organic compounds which contain a thiol group, such as cysteine, methionine and the like. Consequently, one of the advantages of the resulting compounds includes an ability to carefully control both the resulting water and fat solubility of the selenium containing compounds.

A major problem with currently available cancer therapy immunotoxins is the inability to obtain sufficient quantities of cell-surface directed antibodies, problems of nonspecific toxicity and a loss of toxicity associated with the uptake and processing of the immunotoxin conjugate. The use of hybridoma technology has provided the solution to the first problem area, but the other factors mentioned above remain to be adequately resolved. To date, the majority of the immunotoxin studies have concentrated on the use of two readily available toxins: a plant lectin, ricin, and diphtherial toxin produced from bacterial cultures which are commercially available. Typically, these and other toxins enter the cells by binding to the cell surface receptor and enter the cytoplasm following translocation across the membrane, in a manner well known to the art. Once inside, the toxin inhibits protein synthesis through a particular enzymatic reaction.

Accordingly, there currently exists in the art a need to overcome the aforementioned difficulties and provide an immunotoxin which is not only effective against cancer, but is also non-toxic to the host organism being treated. The present invention, by combining a composition such as GSSeSG with a suitable monoclonal antibody, is believed to overcome this problem.

MATERIALS AND GENERAL PROCEDURES

Preparation Of GSSeSG

GSSeSG was synthesized by utilizing a modification of the method of Ganther, reported supra. The purification column was prepared by first preparing a solution containing 32.8g of NaAc, 9.48g $NiCl_2$, and 3.8 liters of double distilled $H_2O$. The resulting solution was adjusted to a pH of 4.7 and then added to 2000 grams of the cationic resin, Dowex-50-X400, so as to obtain a moderately thick slurry. The resulting resin slurry was poured into a 130 cm long, 44 mm inner diameter column maintained at a temperature of 4° C., and the resin was allowed to settle in the column, with the stopcock being kept open so that only a slow drip of solution was able to exit the column. Then, a pump was connected to the base of the column to draw the eluent out of the column and into a spectrophotometer in order to determine exactly when the formed GSSeSG could be collected.

GSSeSG was prepared by forming a solution of 500mg of reduced glutathione obtained from Gallard Schlesinger, Carl Place, NY and 10ml of 0.1 N HCl. The resulting solution was kept on ice, as was a second solution comprising 90mg of $Na_2SeO_3$ and 5ml of 0.1 N HCl, which was also prepared. Upon completion, the glutathione solution was poured into the $Na_2SeO_3$ solution and mixed. The resulting solution was allowed to sit for fifteen minutes, whereupon the pH was adjusted to 4.5 by the addition of 2 M NaAc, and the resulting solution was poured into the purification column.

GSSeSG was purified and concentrated by first removing the nickel from the resin slurry solution of NaAc, $NiCl_2$, $H_2O$, and resin prepared above by adding concentrated NaOH, mixing and then aspirating off the nickel. Upon completion, 0.1 N formic acid was added to the solution until the pH of the resin solution was about 2.6, and the resulting resin solution was poured into the aforementioned small purification column. Again, the resin was allowed to settle with the stopcock open until a slow drip of solution was seen exiting the column. The pump was then attached to the base of the column and hooked up to the spectrophotometer as before. GSSeSG, which had been adjusted to a pH of 3.0 by addition of 5 N HCl, was allowed to slowly drip into the top of the column, being assisted by the pump. At the point where only about a quarter inch of GSSeSG was left on the top of the column, 0.1 N formic acid was slowly poured into the top of the column until several volumes of formic acid had passed through and washed the purification column. Upon completion, 0.1 M Ammonium acetate, having a pH of 5.5, was added by slowly dripping into the top of the column. At the point when the pH of the solution in the column attains a value of 3.3, pure GSSeSG can be produced, ending at a pH of about 4.2. The resulting product was frozen at −20° C. for storage for later usage.

Although not essential to the procedure, assuming it is desired to reuse the column to produce GSSeSG, it is preferred to put the resin in a beaker of 0.1N NaAc, 0.01N NaOH and water until ready to use again, at which time the excess nickel must be removed by swirling, aspirating and adjusting to a pH of 4.7.

CELL CULTURE ASSAY

The purpose of the cell culture assay is a method for measuring at what concentration of the cancer treating agent will inhibit neoplastic cell division or protein synthesis, and thus cause the death of the neoplastic cells. The particular assay technique is a modification of that described by Mosmann, Jour. of Immunol. Meth., 65, 1983, pp. 55-63. The cell lines used for the in vitro assay are:

| | |
|---|---|
| A549 | lung adenocarcinoma |
| HT29 | colon adenocarcinoma |
| TE 671 | medulloblastoma |
| RPMI 7951 | melanoma |
| MCF 7 | breast adenocarcinoma |
| 12-18 | glioma |
| CI | normal fibroblasts (non-neoplastic strain) |
| Keratinocytes | normal keratinocytes from foreskin (non-neoplastic strain) |

The plating density of each cell type used in the assay is set forth below:

| | |
|---|---|
| A549 | 15,000 cells/well |
| HT29 | 1,000 cells/well |
| TE 671 | 1,000 cells/well |
| RPMI 7951 | 30,000 cells/well |
| MCF 7 | 15,000 cells/well |
| 12-18 | 7,500 cells/well |
| CI | 30,000 cells/well |
| keratinocytes | 15,000 cells/well |

The procedure followed involved adding for each cell type 200 microliters of the cell suspension at the concentration determined above, to each well of a 96-well plate. The plates were allowed to incubate for twenty four hours at 37° C. and humidified in the presence of a 5% $CO_2$ atmosphere, whereupon 20 microliters of GSSeSG concentrations ranging from $10^{-8}$ M to $10^{-4}$ M were added to the wells located on the plate. A variety of concentrations of cycloheximide and adriamycin were utilized as a control. The resulting plates were incubated for six days at 37° C., humidified in a 5% $CO_2$ atmosphere and on the final day of the assay, 20 μl were added to each well of [MTT 3-(4,5-dimethyl-thiazol-2-yl)-2,5-diphenyl tetrazolium bromide], obtained from Sigma Cat #M2128. The MTT is prepared by combining 5mg/ml of a phosphate buffered saline (PBS) solution. The resulting plates were allowed to incubate for four hours at 37° C., whereupon the contents of the plate were dumped and blotted dry on a diaper and 100 microliters of DMSO were added to each well in order to dissolve the formazan crystals which were formed through the reduction of MTT by the presence of the active mitochondria within the cell. Upon completion, the optical density of each well was read on an elisa plate reader set at 570nm (test sample) and 630nm (for reference).

The results obtained disclose that if concentrations less than about $10^{-6}$ M of GSSeSG were utilized, a purple solution was obtained, which indicates that a concentration of GSSeSG present will enable the neoplastic cells to survive suggested by the ability of active mitochondria to reduce the yellow MTT solution to a purple formagen solution. However, if concentrations of at least about $10^{-5}$ M of GSSeSG are utilized, the purple solution is not obtained, thus indicating that the concentration of GSSeSG is inhibiting the neoplastic cell division, or protein synthesis, referred to above.

The results set forth above can be more easily seen by viewing FIG. in which a plot of neoplastio cell division or cell protein synthesis is described as a function of the concentration of the preferred selenodithiol GSSeSG. As the graph clearly illustrates, the crisis zone is located between a concentration of $10^{-6}$ M and $10^{-5}$ M, wherein the formerly increasing rate of cell division is substantially reduced to zero. In this crisis zone range of concentrations, all of the human cancer cells listed above, when treated with GSSeSG within the cited concentration range, are essentially prevented from dividing.

An additional advantage not readily apparent from the results of FIG. 1 is that as one increases the concentration of the selenodithiol, e.g., GSSeSG, up to about $10^{-6}$ M, the neoplastic cell division actually increases, thus providing a method to grow cells in a suitable culture. Such a technique is particularly useful if it is desired to grow, e.g., epithelial cells rapidly in order to transplant them to a patient. As can be seen, growing the aforementioned cells in GSSeSG increases the rate of growth so as to enable one to rapidly obtain the desired amount of tissue for, e.g., in the case of a burn victim, or a tissue implant or expedite wound healing. A further use for such a growth factor would be to stimulate the immune system of immunocomprised individuals.

The invention discloses that a small class of selenodithiols including selenodimethionine, selenodicysteine and, most particularly, GSSeSG, can alter the growth of cancerous mammalian and human cells sensitive to treatment with a selenodithiol when appropriate dosages having a very narrow range of effective concentrations are applied. In particular, at concentrations between about $10^{-6}$ M and about $10^{-5}$ M, GSSeSG substantially inhibits proliferation of such neoplastic cells. Indeed at these concentrations all growth is inhibited. When a toxic dose, determined from the absorption constant, K, where K is within the range of ratios from about $10^{-3}$ milligrams of selenodithiol per milliliter of aqueous solution injected per 1.5 centimeters of cancer tumor diameter to about $10^{-3}$ milligrams of selenodithiol per milliliter of aqueous solution injected per 2.5 centimeters of cancer tumor diameter, is administered to the cancer tumor, the radial diffusion of the "dose" causes the selenodithiol to become less toxic at increased distance from the injection site until the concentration nears the concentration of $10^{-6}$ M. Based on the above ratio, and the constant rate of absorption, the diffusion results in a concentration of selenodithiol immediately beyond the cancer tumor periphery in the normal surrounding tissue which is not only unharmful, but which is growth enhancing.

Figure 2:
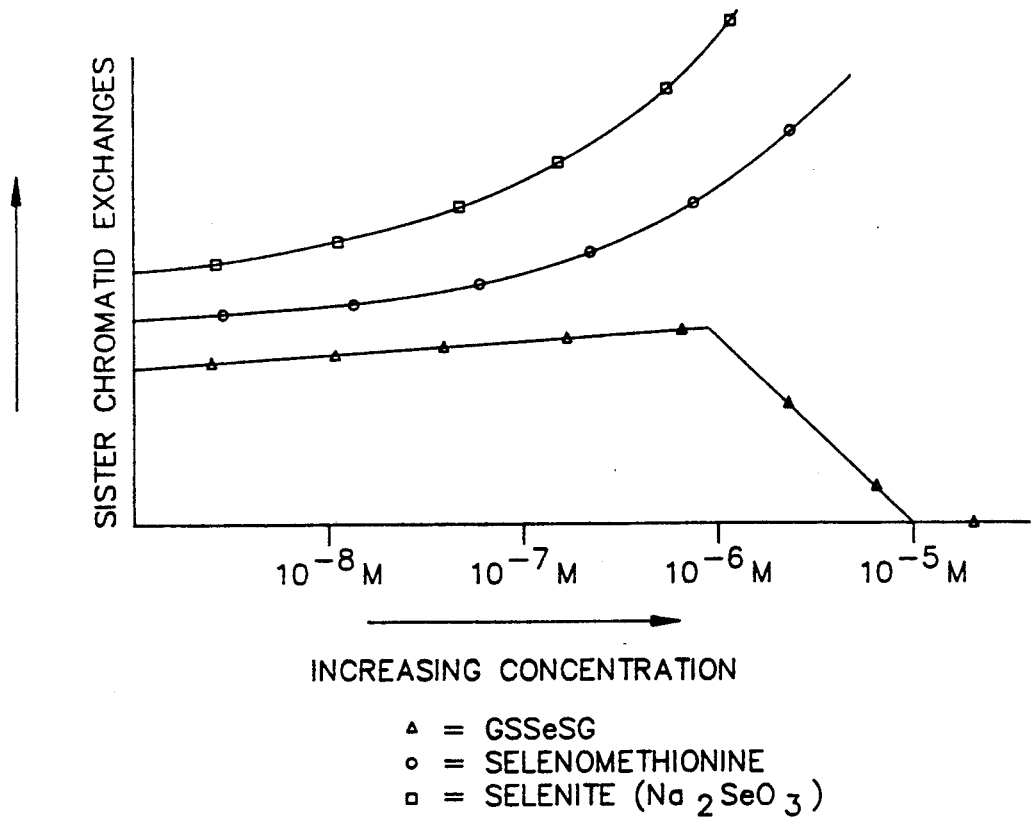
FIG. 2 provides a plot measuring the mutagenicity of three selenium based cancer treating agents as a function of the concentration of each specific agent, one of which is GSSeSG.
Figure 4:
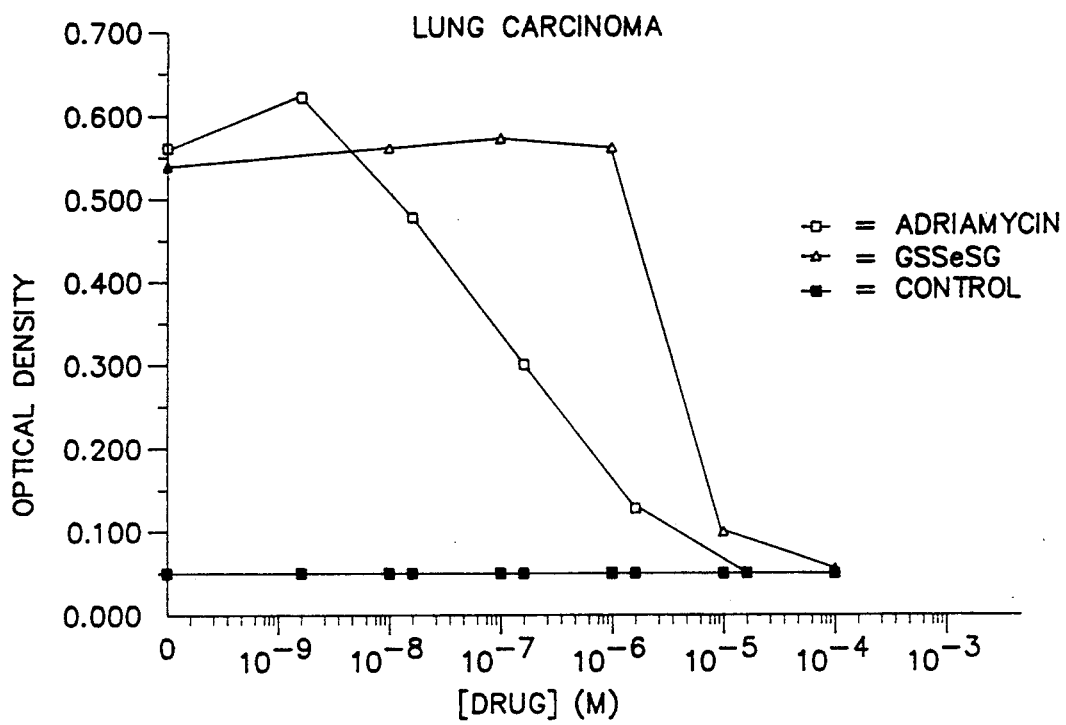
FIG. 4 provides a comparison of the effects at increasing concentrations of adriamycin and GSSeSG as measured by variations in optical density of the cell solution of lung carcinoma.
Figure 5:
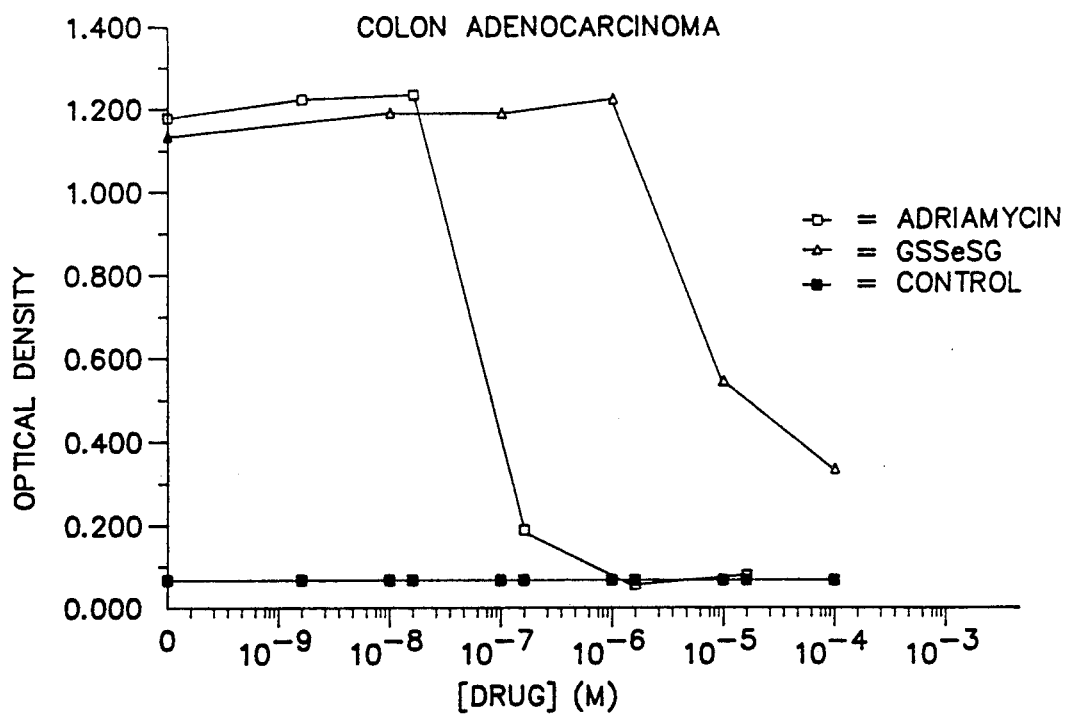
FIG. 5 provides a comparison of the effects at increasing concentrations of adriamycin and GSSeSG as measured by variations in optical density of the cell solution of colon adenocarcinoma.
Figure 6:
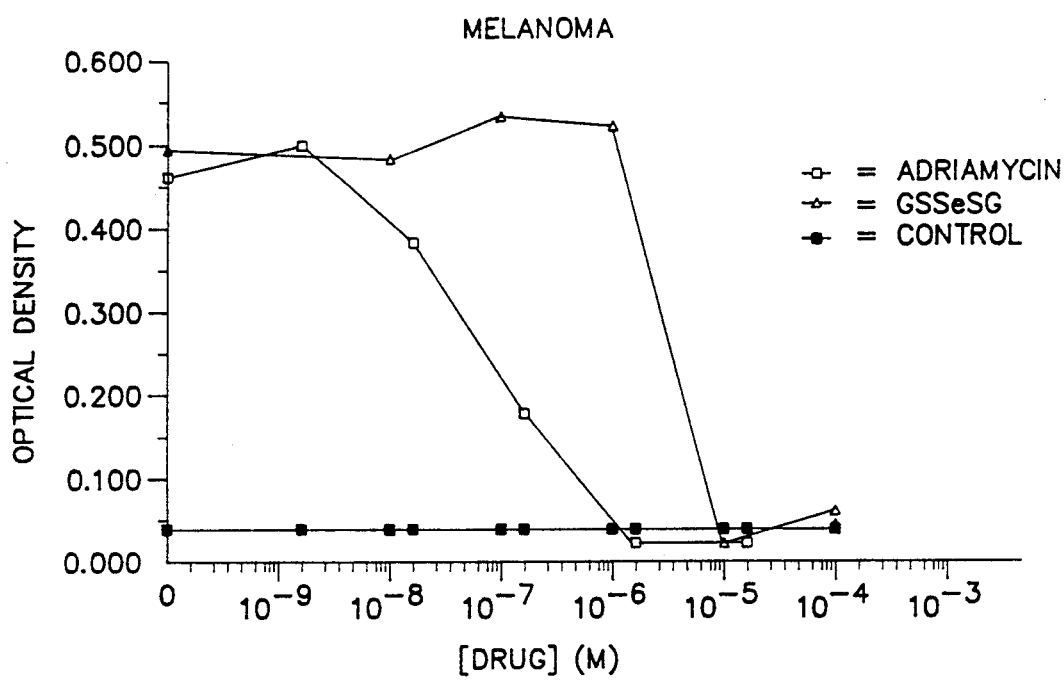
FIG. 6 provides a comparison of the effects at increasing concentrations of adriamycin and GSSeSG as measured by variations in optical density of the cell solution of melanoma.
Figure 7:
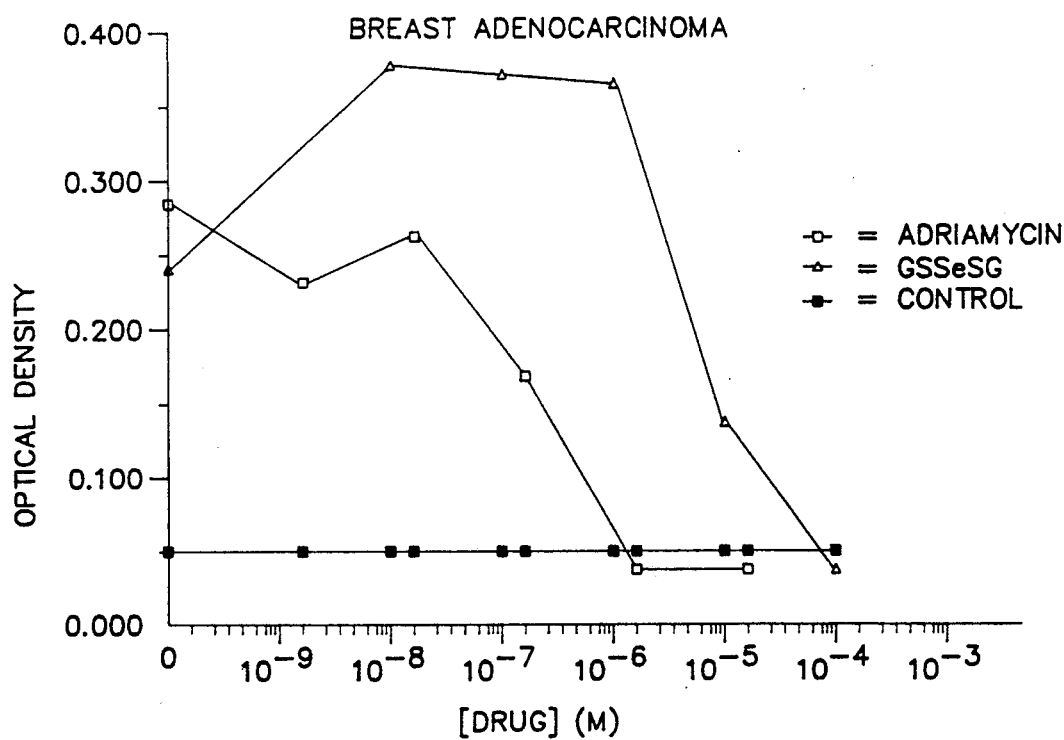
FIG. 7 provides a comparison of the effects at increasing concentrations of adriamycin and GSSeSG as measured by variations in optical density of the cell solution of breast adenocarcinoma.
Figure 8:
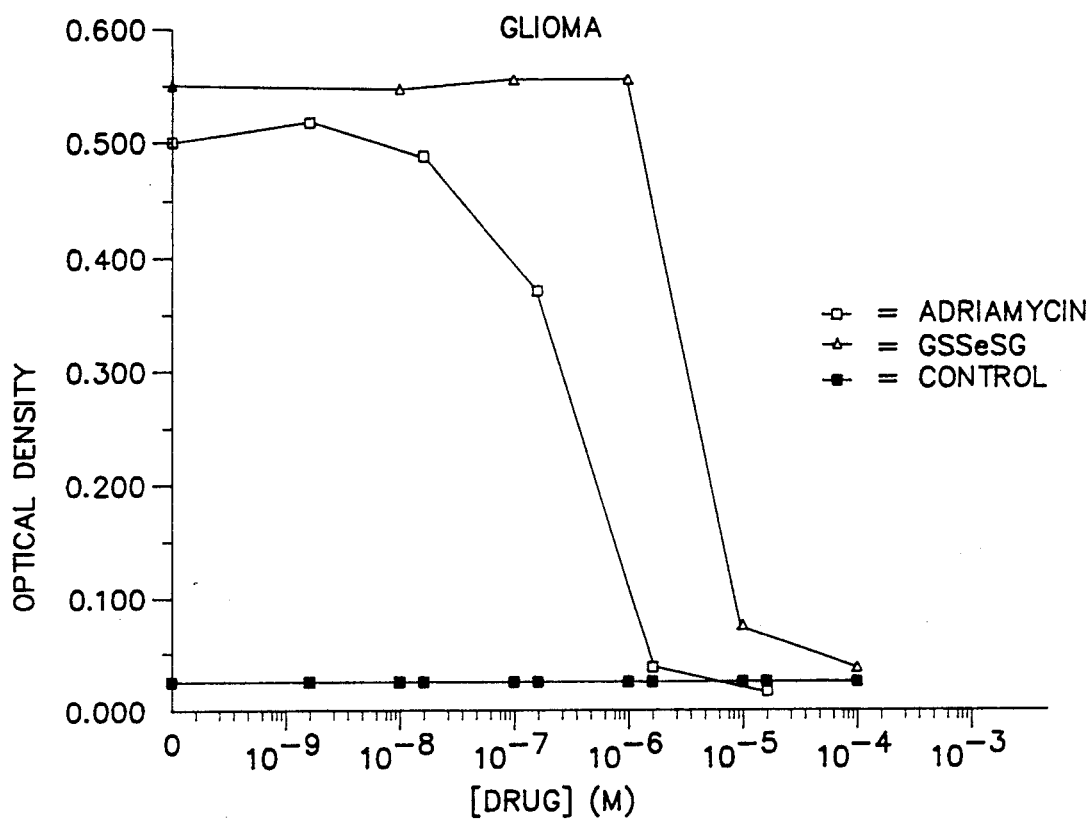
FIG. 8 provides a comparison of the effects at increasing concentrations of adriamycin and GSSeSG as measured by variations in optical density of the cell solution of glioma.
Figure 9:
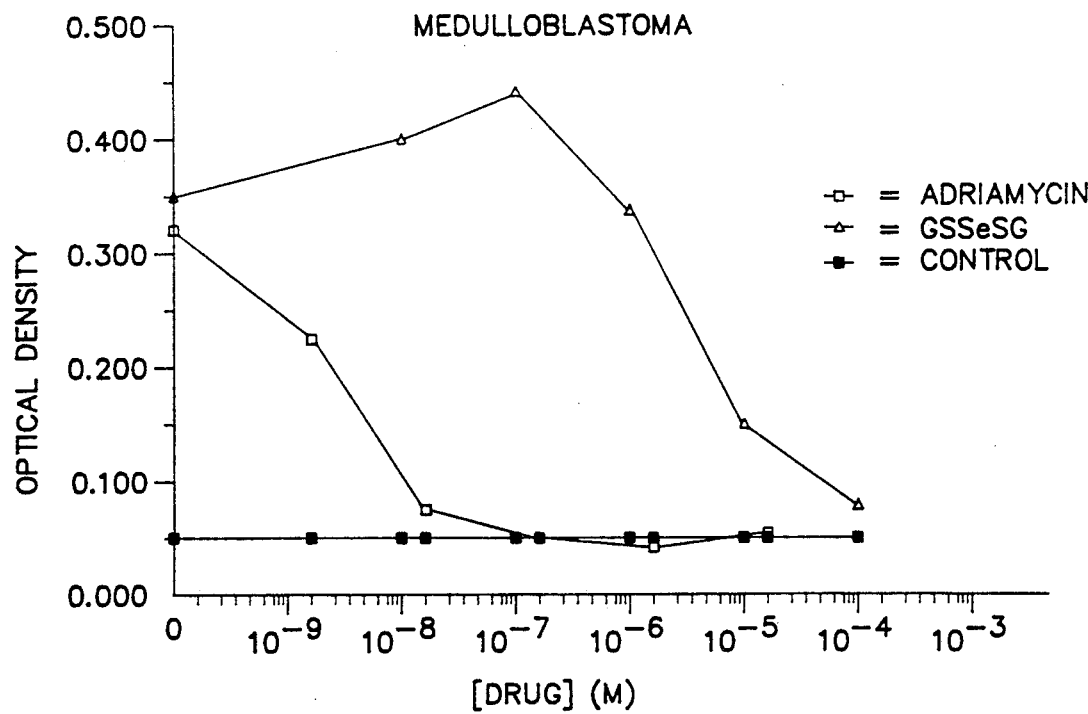
FIG. 9 provides a comparison of the effects at increasing concentrations of adriamycin and GSSeSG as measured by variations in optical density of the cell solution of medulloblastoma.
Figure 10:
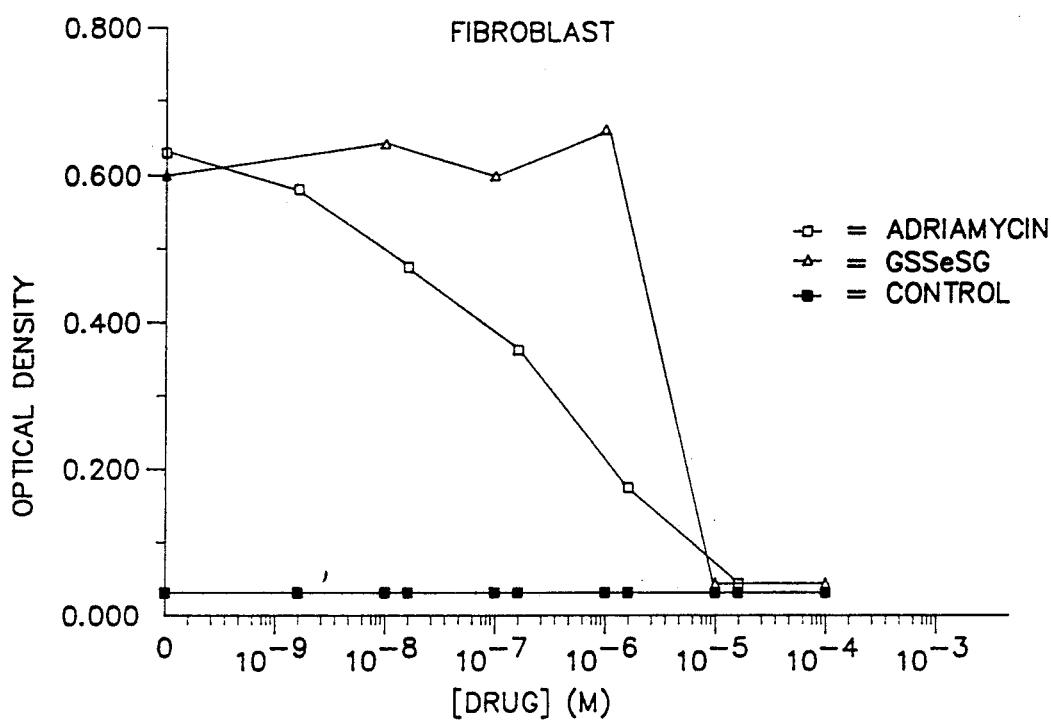
FIG. 10 provides a comparison of the effects at increasing concentrations of adriamycin and GSSeSG as measured by variations in optical density of the cell solution of fibroblast.
Figure 11:
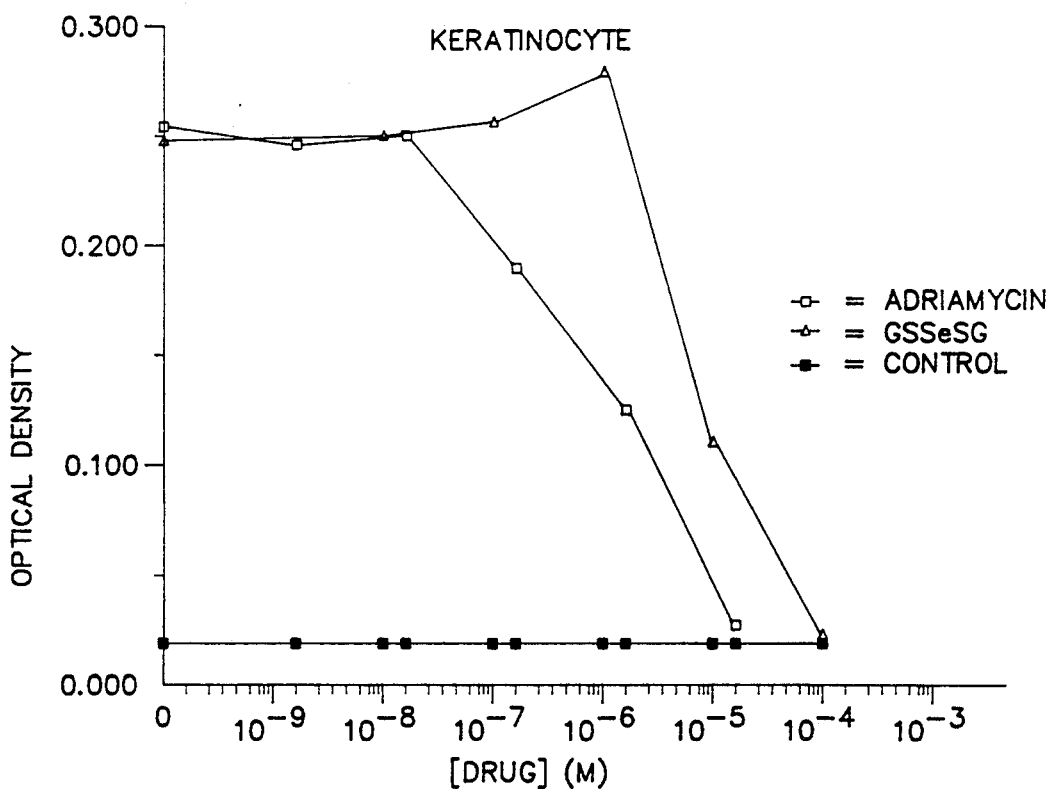
FIG. 11 provides comparison of the effects at increasing concentrations of adriamycin and GSSeSG as measured by variations in optical density of the cell solution of keratinocyte.

FIG. 2 describes the effect that GSSeSG has with respect to the mutagenicity of three selenium containing, cancer treating agents as a function of their respective concentrations. More particularly, the preferred selenodithiol, GSSeSG is contrasted with two other selenium containing compounds, selenite and selenomethionine in the treatment of peripheral blood lymphocytes, i.e., normal human cells taken from different sections of the body. FIG. 2 discloses that the resulting low number of Sister Chromatid Exchanges, which are indicative of a low rate of inducible mutation after treatment with GSSeSG, indicates that the preferred selenodithiol is a far more effective cancer treating agent than the other two anticarcinogens. As one in the art is aware, in the technique known as Sister Chromatid Exchange (SCE) the particular nucleotide components which comprise the DNA genetic code cross over to form cell mutations which lead to the birth and growth of rapidly dividing neoplastic cells.

Thus, the low number of SCE's which are induced by GSSeSG clearly indicates the decreased probability that non-neoplastic cells will spontaneously mutate in the presence of GSSeSG, thereby confirming that GSSeSG will not cause cancer.

Table 1, as seen in FIG. 3, illustrates the particular effectiveness of GSSeSG when administered in the crisis zone dosage range to a group of ten rats. The Table contrasts the results obtained by the desired dosage with the results obtained from four other groups of ten rats; the rats in each group being inoculated with cancer immunotoxins in differing dosages of both GSSeSG, retinol (HPR) and mixtures of each, as well as a control sample of fifty rats which were not administered with cancer treating agents. All one hundred rats were inoculated with DMBA (7,12-dimethylbenz(a)anthracene) so as to induce cancer cell formation, which was then allowed to form tumors over a period of two months prior to testing. It is seen that the control rats were fed a normal diet and had an average weight of 241 grams. One group of ten rats were injected with 2 μg of GSSeSG per gram of bodyweight and presently all but one of these specimens are dead at seventy nine days. However, cutting the GSSeSG concentration in half resulted in moving the effective concentration to the lower end of the aforementioned "crisis zone" range, thereby enabling GSSeSG to inhibit cancer cell proliferation within the rats without creating an accompanying toxic effect (note the high body weights). Thus, the administration of GSSeSG at 1 μg per gram of rat body weight not only resulted in the substantial elimination of the cancer cells but, as indicated by their bodyweight, resulted in substantially no harm to the rats. The other three groups of rats disclose the administration of GSSeSG mixed with the cancer treating agent retinol, as well as one test sample of just retinol, but while the anticarcinogens were effective in arresting the cancer, they also caused severe damage to the rats, as can be seen by the bodyweight column. Thus, Table 1 clearly illustrates both the effectiveness of GSSeSG when utilized in the desired range of proportions and also the fact that even relatively small variations in excess of the crisis zone in its administration will cause severe damage to the host subject, while the proper range of dosages is substantially non-toxic to the treated host.

FIGS. 4 through 11 provide comparisons of the effects at increasing concentrations of adriamycin and GSSeSG as measured by variations in optical density of various cell solutions. The FIGS. illustrate that GSSeSG has a dramatic effect on cell division within the claimed concentration range. This was achieved using the microculture tetrazolium assay technique of Mosmann (J. Immun. Meth., 65, 1983, pp. 55-63). This technique measures the effectiveness of experimental chemotherapeutic agents on various human tumor cell lines. Mitchondrial enzymes of active tumor cells have the capacity to reduce a yellow tetrazolium solution to a blue formazan product. Variations in optical density, measured by a spectrophotometer, are indicative of the level of cellular activity. FIGS. 4 through 11 show the effects of GSSeSG, compared to adriamycin, at varying concentrations on reducing the level of cellular activity. The results of these FIGS. demonstrate that all cell lines responded to GSSeSG in a biphasic manner, i.e., for concentrations from $10^{-8}$ Molar to $10^{-6}$ Molar, activity was enhanced and for concentrations between $10^{-6}$ Molar and $10^{-5}$ Molar activity was significantly inhibited, indicating cytoxic levels.

Figure 12:
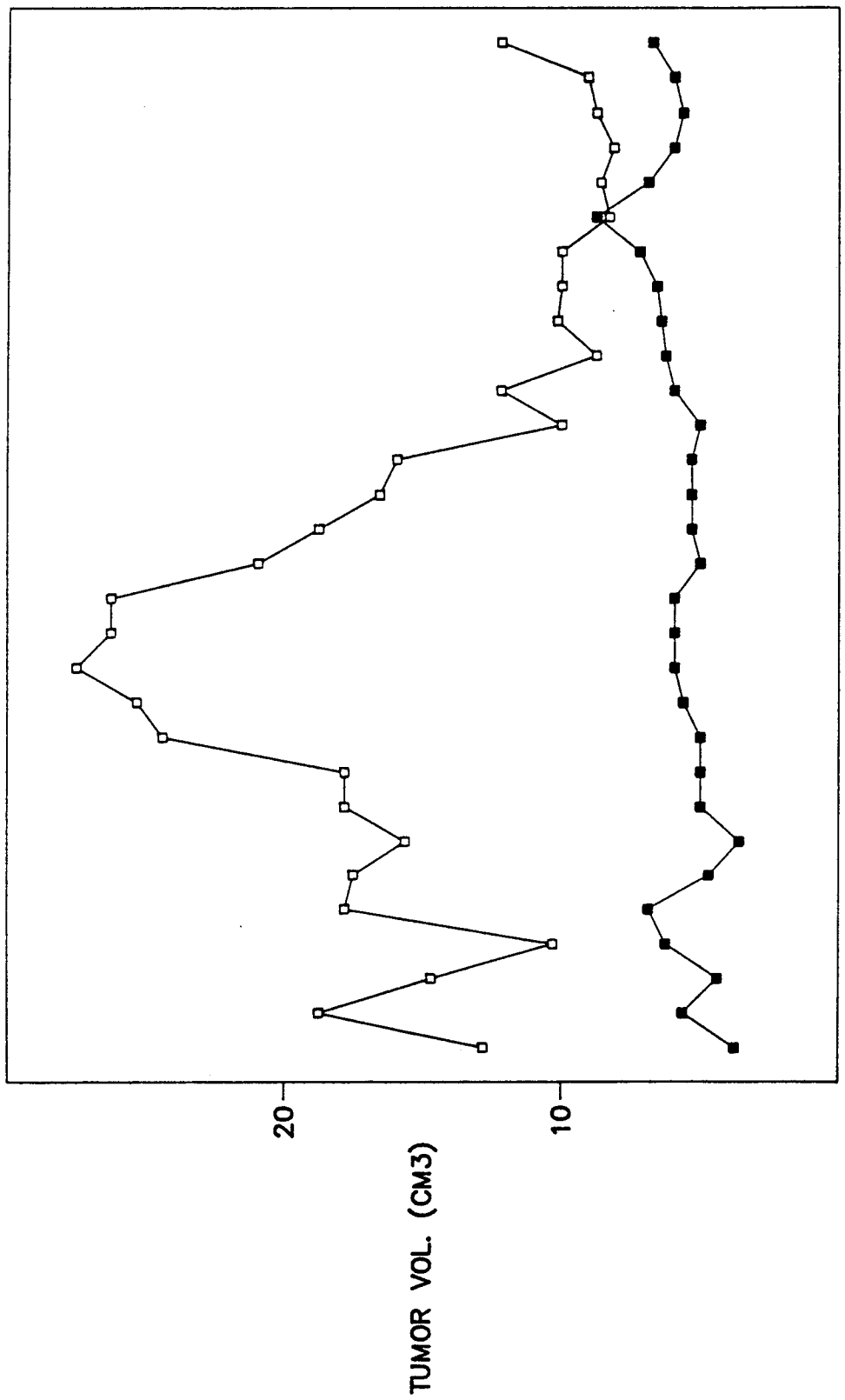
FIG. 12 shows the effect of selenodiglutathione on the reduction of the size of rat mammary tumor when injected directly into the tumor.

FIG. 12 shows the effect of selenodiglutathione on the reduction of the size of rat mammary tumor when injected directly into the tumor every other day. The tumor was induced in each rat by the administration of 7,12-dimethylbenz(a)anthracene and allowed to proliferate to the predetermined sized range of 1.5 to 2.5 centimeters in diameter. The selenodiglutathione was injected at a level of 700 micrograms directly into the central region of the tumor mass fifteen times over the course of thirty days. The growth of the control tumor, which did not receive selenodiglutathione, is shown in the lower curve while the upper curve depicts the growth of the mammary tumor injected with selenodiglutathione. As can be seen, there was initially some growth of the overall size of the tumor injected with the selenodiglutathione as the outer portions of the tumor exhibited cell proliferation. Eventually, as the concentration of the selenodiglutathione reached the levels claimed herein, the tumor's size decreased dramatically until it became hard and calcified. This demonstrates an effective reduction in the size of the cancer tumor without any detrimental effect to the animal itself.

Figure 13:
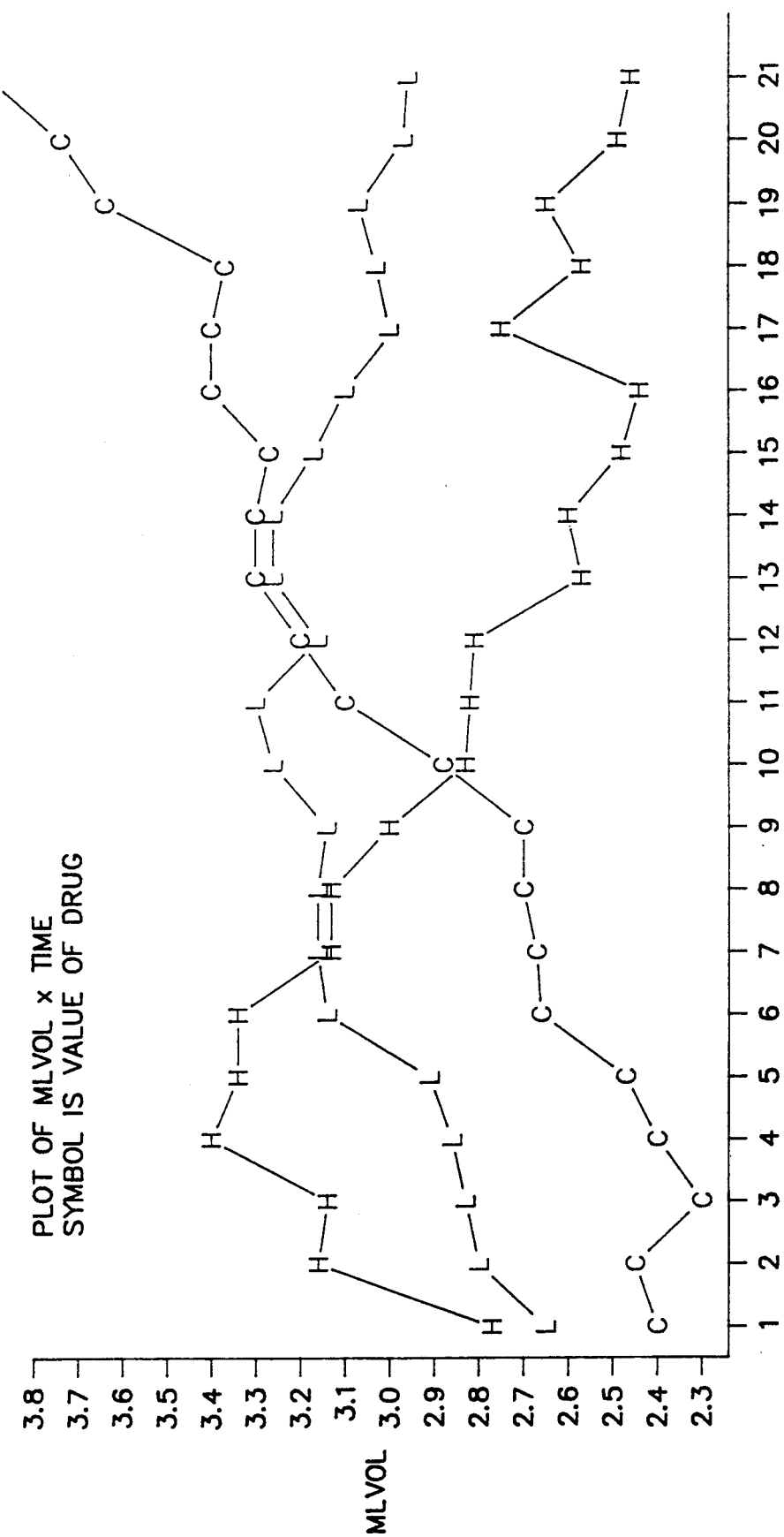
FIG. 13 illustrates a table comparing the volume changes of two rat mammary cancer tumors injected repeatedly over time with GSSeSG to the volume changes of a rat mammary cancer tumor injected with aqueous solution without GSSeSG.

FIG. 13 illustrates a table comparing the volume changes of three rat mammary cancer tumors injected over time. The curve marked "C" represents the volume increase in a control tumor injected with eluate from the column but with no selenodithiol. Curves "L" and "H" represent cancer tumors injected according to different treatment schedules of selenodiglutathione. The "L" tumor received a dose of selenodiglutathione of 1.46cc of $7 \times 10^{-3}$ M every forty eight hours for twenty eight days while the "H" tumor received a dose of selenodiglutathione of 2.8cc of $7 \times 10^{-3}$ M every ninety six hours for twenty eight days. As can be seen from FIG. 13, "L" and "H" tumors initially increased in volume as the concentration of selenodiglutathione was promoting cell proliferation in the tumor periphery. Eventually, both these mammary tumors stopped growing and the H tumor decreased in volume to a level significantly below the initial volume. The control tumor, C, continued to increase in volume dramatically.

Repeated injections over a period of time are generally required to achieve the desired reduction in tumor size according to the present invention. As a result of the biphasic effect, initially the tumor may actually grow in size depending on the concentration of selenodithiol administered. However, with repeated injections or cannulations of the selenodithiol to the cancer tumor comprising cells sensitive to treatment with selenodithiol, a toxic level is eventually attained in the tumor resulting in the reduction or death of the tumor.

It has further been discovered that rats which are injected with effective dosages of GSSeSG at site distant from the tumor will still kill the cancer tumors. This was demonstrated by the disappearance of secondary superficial tumors that were located a distance from the point of injection of GSSeSG.

The compounds of this invention will generally be administered to animals, including but not limited to, mammals including humans. In the broadest embodiment, it is believed that any cell containing EF-2 can be inhibited by GSSeSG; thus, the compositions of the invention are effective against all eucaryotic cells, i.e., mammalian neoplasms, including chemically induced as well as naturally induced cancerous cells.

Additionally, it is believed that the active compounds of this invention can be processed in accordance with conventional methods of galenic pharmacy to produce appropriate medicinal agents for administration to the desired host patient.

The compounds of this invention can be employed in a mixture with conventional excipients, i.e. pharmaceutically acceptable, organic or inorganic carrier substances suitable for parenteral, injection or oral application which do not deleteriously react with the active compounds. Suitable pharmaceutically acceptable carriers include, but are not limited to water, salt solutions, alcohols, gum arabic, vegetable oils, benzyl alcohols, polyethylene glycose, gelatine, carbohydrates such as lactose, amylose, or starch, magnesium stearate, talc, silicic acid, viscous paraffin, perfume oil, fatty acid monoglycerides, and diglycerides, pentaerythritol fatty acids esters, hydroxy methylcellulose, pyrrolidone, etc. The resultant preparations can be sterilized and, if desired, mixed with an auxiliary agent, e.g. lubricants, preservatives, stabilizers, wetting agents, emulsifiers, salts for influencing osmotic pressure, buffers, coloring, flavoring and/or aromatic substances and the like which do not deleteriously react with the active compounds. They can also be combined or desired with other active agents, e.g. vitamins.

Although it has been indicated above that a particularly narrow concentration range is not only preferred, but essential, it should also be appreciated that the actual preferred amounts of active compound in a specific case can vary according to the specific compound being utilized, the particular composition formulated, the mode of application, and the particular size and organisms being treated. Within the absorption constant range provided herein, dosages for a given host can be determined using conventional considerations, e.g., by customary comparison of the differential activities of the subject compound and of a known agent.

From the foregoing description, one skilled in the art can easily ascertain the essential characteristics of this invention, and without departing from the spirit and scope thereof, can make various changes and modifications of the invention to adapt it to various usages and conditions.

While certain preferred embodiments of the present invention have been disclosed in detail, it is to be understood that various modifications may be adopted without departing from the spirit of the invention or scope of the following claims.

We claim:

1. A biphasic method of treating cancer tumors sensitive to treatment with a selenodithiol selected from the group consisting of selenodiglutathione, selenodicysteine, and selenodimethionine, wherein the method comprises a first phase administering an effective amount of the selenodithiol directly into the central region cf a cancer tumor, wherein the effective amount of the selenodithiol is an amount sufficient to achieve an initial concentration in the tumor of from about $10^{-3}$ milligrams of selenodithiol per milliliter of aqueous solution administered per 1.5 centimeters of tumor diameter to about $10^{-3}$ milligrams of selenodithiol per milliliter of aqueous solution administered per 2.5 centimeters of tumor diameter, wherein said tumor diameter is the average of the tumor's major and minor axis lengths measured in centimeters, whereby the proliferation of the cells in the tumor sensitive to treatment with selenodithiol is inhibited, and whereby in a second phase the selehodithiol further diffuses outwardly through the tumor from the central site of administration to the periphery of the tumor, and further diffuses into the surrounding non-cancerous tissue at a concentration of less than about $10^{-6}$ M.

2. The method of claim 1 whereby the cell growth of cells sensitive to treatment with selenodithiol in the surrounding non-cancerous tissue is stimulated to an increased rate.

3. The method of claim 1 wherein the administration of the selenodithiol into the central region of the cancer tumor is by means of injection.

4. The method of claim 1 wherein the administration of the selenodithiol into the central region of the cancer tumor is by means of cannulation.

5. A method for the biphasic treatment of cancer cells and surrounding non-cancerous tissue in a mammal, wherein the first phase of the biphasic treatment comprises the administration to the central region of a tumor of cancer cells in the mammal of a selenodithiol selected from the group consisting of selenodicysteine, selenodimethionine, and selenodiglutathione, whereby the ratio of selenodithiol to tumor volume is in the range of about $10^{-3}$ milligrams of selenodithiol per milliliter of aqueous solution administered per 1.76 cubic centimeters of tumor to about $10^{-3}$ milligrams of selenodithiol per milliliter of aqueous solution administered per 8.18 cubic centimeters of tumor, whereby proliferation of the cancer cells sensitive to treatment with the selenodithiol is inhibited, said selenodithiol radiating outwardly from said central region of the tumor by diffusion, and wherein a second phase of the biphasic treatment comprises the outwardly radiating diffusion of said selenodithiol in the tumor to said noncancerous surrounding tissue of the mammal, wherein the concentration of the selenodithiol in the second phase in said non-cancerous surrounding tissue is reduced by the diffusion to a concentration below about $10^{-6}$ M, whereby proliferation of the cells sensitive to treatment with the selenodithiol in said non-cancerous surrounding tissue is enhanced, and whereby the mammal is not adversely effected by said biphasic treatment.

6. The method of claim 5 wherein the tumor in the mammal is a cancer tumor selected from the group consisting of lung adenocarcinoma, colon adenocarcinoma, medulloblastoma, melanoma, breast adenocarcinoma, glioma, and keratinocytes.

7. A method for the biphasic treatment of cancer cells and the surrounding tissue inn a mammal, wherein a first phase of the biphasic treatment comprises the administration to a site of cancer cells in the mammal of a selenodithiol selected from the group consisting of selenodiglutathione, selenodicysteine, and selenodimethionine at a concentration above about $10^{-6}$ M, whereby proliferation of the cancer cells sensitive to treatment with the selenodithiol is inhibited, said selenodithiol radiating outwardly from said site by diffusion, and wherein a second phase of the biphasic treatment comprises the outwardly radiating diffusion of said selenodithiol in the cancer cells to said surrounding tissue of the mammal, wherein the concentration of the selenodithiol in the second phase in said surrounding tissue is reduced by the diffusion to a concentration below about $10^{-6}$ M, whereby proliferation of the cells sensitive to treatment with the selenodithiol in said surrounding tissue is enhanced, and whereby the mammal is not adversely effected by said biphasic treatment.

8. The method of claim 7 wherein the site inn the mammal of administration of the selenodithiol is a cancer tumor selected from lung adenocarcinoma, colon adenocarcinoma, medulloblastoma, melanoma, breast adenocarcinoma, glioma, and keratinocytes.

* * * * *

UNITED STATES PATENT AND TRADEMARK OFFICE
CERTIFICATE OF CORRECTION

PATENT NO.  : 5,104,852
DATED       : April 14, 1992
INVENTOR(S) : Francis A. Kralick et al.

It is certified that error appears in the above-identified patent and that said Letters Patent is hereby corrected as shown below:

In column 4, line 55, after "provides", insert --a--. In column 5, line 24, after "in" and before "so-called", insert --a--; line 41, "biphasio" should read --biphasic--. In column 6, line 52, after "V", insert --=--; line 63, "176" should read --1.76--. In column 7, line 27, insert period mark after end of paragraph; line 46, "noncancerous" should read --non-cancerous--; line 67, after "$10^{-6}M$", insert period mark. In column 11, line 27, after "FIG.", insert --1--; line 27, "neoplastio" should read --neoplastic--. In column 14, line 16, after "at" insert --a--. In claim 1, column 15, line 17, "cf" should read --of--; line 29, "selehodithiol" should read --selenodithiol--. In claim 5, column 16, line 11, "noncancerous" should read --non-cancerous--. In claim 7, column 16, line 27, "inn" should read --in--. In claim 8, column 16, line 46, "inn" should read --in--.

Signed and Sealed this

Twenty-second Day of June, 1993

Attest:

MICHAEL K. KIRK

Attesting Officer

Acting Commissioner of Patents and Trademarks